(12) United States Patent
Dosmann et al.

(10) Patent No.: US 8,377,381 B2
(45) Date of Patent: Feb. 19, 2013

(54) OPTICAL FORMAT

(75) Inventors: Andrew J. Dosmann, Granger, IN (US); Frank W. Wogoman, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 1963 days.

(21) Appl. No.: 10/750,271

(22) Filed: Jan. 2, 2004

(65) Prior Publication Data

US 2004/0142370 A1    Jul. 22, 2004

Related U.S. Application Data

(60) Provisional application No. 60/440,859, filed on Jan. 21, 2003.

(51) Int. Cl.
*G01N 21/00* (2006.01)
*G02B 6/26* (2006.01)
*G01N 33/48* (2006.01)

(52) U.S. Cl. ............ 422/82.11; 422/82.05; 356/39; 356/40; 356/41; 356/42; 385/15; 385/36; 385/39; 385/47; 385/50

(58) Field of Classification Search ............ 356/39, 356/40, 41, 42; 422/55, 73, 82.05, 82.11
See application file for complete search history.

(56) References Cited

U.S. PATENT DOCUMENTS

| 3,141,094 A | 7/1964 | Strickler | |
|---|---|---|---|
| 4,710,623 A | 12/1987 | Lipson et al. | 250/227 |
| 4,725,150 A | 2/1988 | Ishida et al. | 374/170 |
| 4,803,992 A | 2/1989 | Lemelson | 128/634 |
| 5,418,615 A | 5/1995 | Doyle | |
| 5,525,518 A | 6/1996 | Lundsgaard et al. | 436/68 |
| 6,001,307 A | 12/1999 | Naka et al. | 422/81 |
| 6,014,577 A | 1/2000 | Henning et al. | 600/345 |
| 6,216,022 B1 * | 4/2001 | Tyrrell et al. | 600/310 |
| 2001/0027277 A1 | 10/2001 | Klitmose | |
| 2003/0157724 A1 | 8/2003 | Petrich et al. | |
| 2004/0091394 A1 | 5/2004 | Brenneman | 422/58 |

FOREIGN PATENT DOCUMENTS

| EP | 0 254 246 A2 | 1/1988 |
|---|---|---|
| EP | 0 294 650 A | 12/1988 |
| JP | 6050 1622 T | 9/1985 |
| JP | 61159121 A | 7/1986 |
| JP | 09-308624 A | 12/1997 |
| JP | 2000504239 T | 4/2000 |
| WO | WO 88/01376 | 2/1988 |
| WO | WO 01/48461 A1 | 7/2001 |
| WO | WO 01/72225 A1 | 10/2001 |

* cited by examiner

*Primary Examiner* — Neil N Turk
(74) *Attorney, Agent, or Firm* — Nixon Peabody LLP

(57) ABSTRACT

An optical waveguiding optical format enables consistent optical analysis of small sample volumes. The optical format is comprised of an illumination light guide, a read window upon which a sample is placed, a sample collection needle or capillary, and a detection guide. Light redirecting facets are provided within the format itself such that the format serves as a unitary component for accepting light, directing light through a sample, and emitting light for detection.

28 Claims, 2 Drawing Sheets

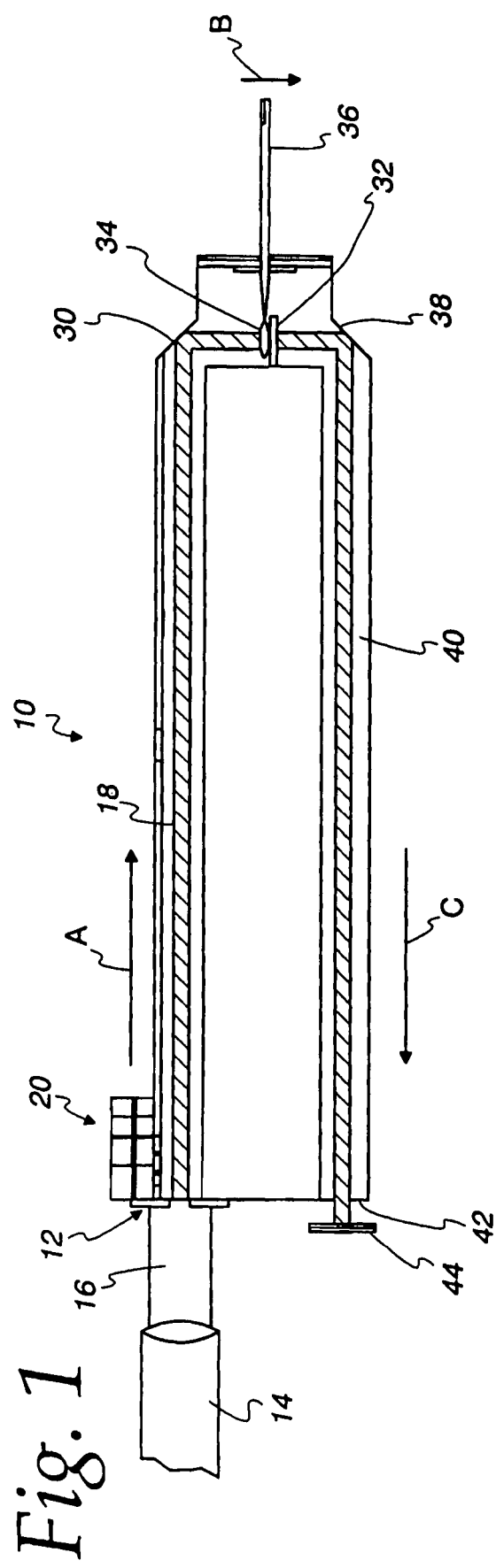
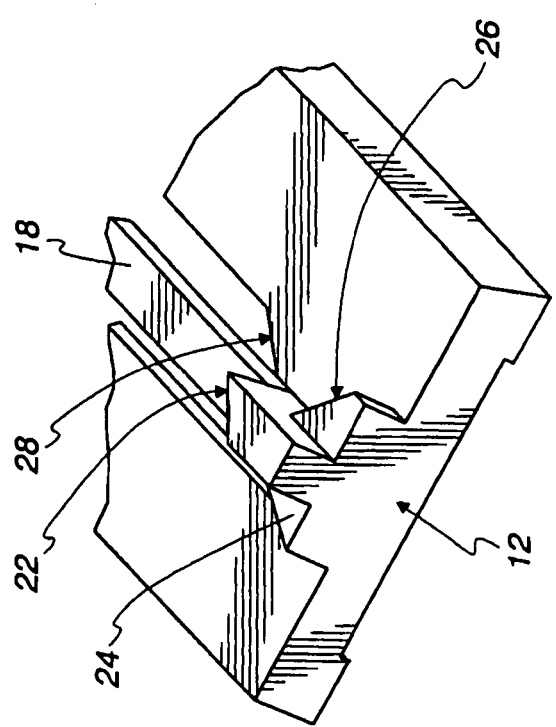

OPTICAL FORMAT

CROSS-REFERENCE TO RELATED APPLICATION

This application claims benefit to U.S. Provisional Application No. 60/440,859, filed on Jan. 21, 2003.

FIELD OF THE INVENTION

The present invention relates generally to medical testing and more specifically to optical analysis of fluids using a molded optical format.

BACKGROUND OF THE INVENTION

In recent years, various types of medical analysis have become increasingly decentralized and more accessible to the patient. The testing of bodily fluids represents one example of this decentralization. Many tests that previously had to be performed at a doctor's office and perhaps even analyzed at a separate office can now be performed immediately and inexpensively in the comfort of a patient's home. One example of such a test is blood glucose monitoring, which is widely used among diabetic patients.

Optical analysis has presented itself as one convenient method for analyzing bodily fluids. In a typical optical analysis application, a certain amount of fluid is placed in a read area adapted to allow light to pass through the fluid. The light transmitted through the fluid can then be collected and analyzed, with changes in the light indicating medically significant properties of the fluid. Fluid may be directed to a read area using a "format," or a platform for collecting and handling the fluid.

A problem arises in that the fluid volumes used for such analyses is very small-typically in the range of from about 50 nl to about 250 nl. Such a small sample volume calls for the use of a small read area or window upon which the sample is placed and through which light is passed for analysis. For example, an optical read area of about 1.0 mm is appropriate in many applications.

One result of using a small window is that a smaller optical read diameter is necessary to avoid reading the edge of the window when the goal is to take an optical reading of the sample. For example, with a 1.0 mm window, an optical read area of about 0.75 mm might be appropriate to avoid reading the window edge.

Typically, the small window and optical read diameters of optical fluid testing systems call for tight mechanical tolerances between the format and the illumination and reading device or devices, and further require a narrow light beam to ensure the beam always passes through the read window where the sample is located. For the example given above, a typical mechanical tolerance of ±0.381 mm (a combined tolerance of ±0.254 mm for the optics and format) is needed between the format and optics. When the alignment tolerances are taken into consideration, a beam diameter of only 0.369 mm (0.75 mm-0.381 mm) is required to ensure that the beam always passes through the window. It is desirable to have an easy-to-use format for the optical testing of fluids which allows for increased tolerances between the format and optics, and which further allows for the use of a wider-diameter illumination beam.

A further problem with self-testing small amounts of sample is the lack of a convenient method of lancing, harvesting, and analyzing small sample volumes. Sample volumes of 50 to 250 nl are too small for the consumer to easily see and too difficult to place into an optical format. This problem leads to the desirability of an easy-to-use format for optical testing of fluids that enables convenient harvesting of samples.

SUMMARY OF THE INVENTION

According to one embodiment of the present invention, a single waveguiding optical format accepts illumination, directs the illumination through a fluid sample, and further directs the resulting output light out of the format and toward a detector.

According to another embodiment of the present invention, a molded optical format for optical analysis of low-volume fluid samples comprises an illumination input and an illumination guide which accepts light from the illumination input and directs it toward an optical read window. The format further includes a detection guide which guides the light toward a detection output, where the light is emitted from the format and directed toward a detector.

According to still another embodiment of the present invention, a method for performing optical analysis of a fluid uses a single optical format to collect and store a fluid sample and further directs light through the format and fluid sample and then out of the format. Overillumination redirection facets redirect overilluminating light away from the format.

BRIEF DESCRIPTION OF THE DRAWINGS

FIG. 1 is a side view of an optical format according to one embodiment of the present invention;

FIG. 2 is an isometric view of an overillumination redirection component according to one embodiment of the present invention;

Figure 3:
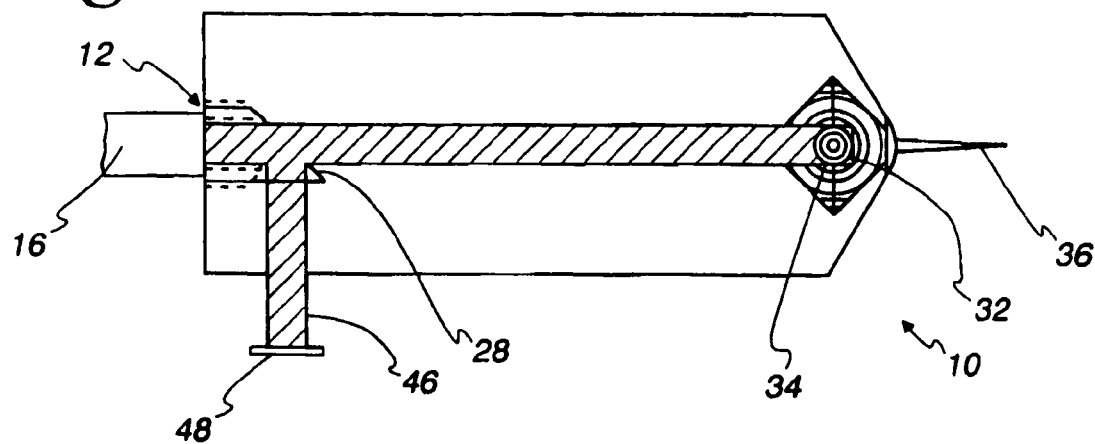
FIG. 3 is a top view of an optical format according to one embodiment of the present invention.

While the invention is susceptible to various modifications and alternative forms, specific embodiments are shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DESCRIPTION OF SPECIFIC EMBODIMENTS

In optical testing of fluids for medical purposes, such as the transmission spectrophotometry of blood or interstitial fluid for glucose concentration measurements, instruments and techniques which reduce the complexity of the required medical devices or provide for easier interaction with the user are of great value. Turning to FIG. 1, an optical format 10 capable of significantly reducing the complexity of design for optical testing instruments and further increasing ease of testing is shown. The optical format 10 includes an illumination input area 12 which accepts light from a light source 14. The light source may be a laser such as a diode laser, or any other type of light source used in medical fluid analysis. According to one embodiment of the present invention, a collimated input beam 16 is used to illuminate the illumination input area 12. According to one embodiment, the input beam 16 has a cross-sectional area of about 1.0 mm². It is preferred for the light beam to underfill the illumination input area 12 and overfill an illumination light guide 18. According to one embodiment of the optical format 10, the illumination input area 12 has a cross-sectional area of about 1.5 mm² and the illumination light guide 18 has a cross-sectional area of about 0.5 mm².

When the format 10 is in use, light is guided from the illumination input area 12 in the direction shown by the arrow "A" by an illumination light guide 18. The illumination input area 12 guides the input beam 16 to an overillumination redirection component 20 which serves to redirect overilluminating light away from the direction of light travel through the illumination light guide 18. As more clearly seen in FIG. 2, according to one embodiment of the present invention, the overillumination redirection component 20 includes first, second, third, and fourth overillumination redirection facets 22, 24, 26, and 28. Unnecessary over-illuminating light may interfere with the accuracy of sample reading, and is thus directed away from the optical format 10. The overillumination redirection facets 22, 24, 26, and 28, reflect the input light via total internal reflection to redirect the over-illuminated portion of the input illumination approximately perpendicular to the illumination light guide 18. According to one embodiment of the present invention, alignment of the input beam 16 to the input of the illumination light guide 18 can be altered within ±0.25 mm without under-illuminating the illumination light guide 18.

FIG. 2 shows an illumination redirection arrangement according to one embodiment of the present invention having four overillumination redirection facets. Each overillumination redirection facet is positioned to redirect overilluminating light away from the illumination light guide, with certain facets redirecting overillumination from respective areas of an overilluminating beam. In the embodiment shown in FIG. 2, a first overillumination redirection facet 22 redirects overilluminating light from the top of an input beam 16 away from the illumination light guide 18. In the embodiment shown in FIG. 2, a first overillumination redirection facet 22 is positioned to redirect overilluminating light from the top of an input beam (top, down, left, and right directions are given from the point of view as seen in FIG. 2) to the right of the direction of travel of the input beam 16, though it is contemplated that the first overillumination redirection facet 22 could redirect overilluminating light from the top of the input beam 16 in another direction. FIG.2 shows the second overillumination redirection facet 24 disposed to redirect overilluminating light from the left side of the input beam 16 toward the right of the direction of travel of the input beam 16. The third overillumination redirection facet 26 is shown in FIG. 2 disposed to redirect overilluminating light from the right side of the input beam 16 toward the left of the direction of travel of the input beam 16. The fourth overillumination redirection facet 28 is shown in FIG. 2 disposed to redirect overilluminating light from the bottom side of the input beam 16 toward the right of the direction of travel of the input beam 16. It is contemplated that each of the overillumination redirection facets 22, 24, 26, and 28 may be disposed to redirect overilluminating light in other directions, including above and below the direction of input, and away from rather than through the input beam, depending on particular applications of the optical format 10. More or fewer redirection facets may be employed as required by specific optical format embodiments. Any of the overillumination redirection facets may be employed to redirect a portion of the input beam 16 for use as a reference beam. As is discussed below in connection with FIG. 3, according to one embodiment of the present invention the fourth overillumination redirection facet reflects a reference beam.

An input illumination redirection facet 30 reflects the input light via total internal reflection in the direction shown by arrow "B." According to one embodiment of the present invention, the illumination redirection facet 30 is coated with a reflective material. According to one embodiment of the invention, the illumination redirection facet 30 is disposed at a 45-degree angle relative to the illumination light guide 18.

According to the embodiment shown in FIG. 1, following reflection from the input illumination redirection facet 30, the input light is directed through a read window 32 containing a fluid sample 34. Guiding light through the format 10 and onto the sample 34 allows less sample volume to be analyzed and provides a more convenient means of harvesting extremely small sample volumes. According to one embodiment of the optical format 10, a sample 34 is directed onto the read window 32 via a needle 36 or capillary. A needle 36 may be used to lance the patient and harvest a sample with one action; integrating the lancing and harvest of a sample greatly simplifies operation for a patient. The read window 32 serves as an optically clear platform upon which the fluid sample to be tested is accurately positioned with respect to the illumination light guide 18 and the illumination redirection facet 30. According to one embodiment of the present invention, a reagent is dried onto the read window 32. In this embodiment, the reagent is reconstituted with the sample to provide a colormetric change in the sample.

According to one embodiment of the invention, the optical read area through which the input light passes is optimized to average imperfections in the read window 32, average non-uniform color development in a sample, and increase signal levels at a signal detector. Following the interaction between the light and the sample 34 at the read window 32, the light may be termed "detection light."

Following interaction with the sample 34, the detection light is redirected by a detection redirection facet 38 in the direction shown by the arrow "C" into a detection guide 40. According to one embodiment of the invention, the detection redirection facet 38 is disposed at a 45-degree angle relative to the detection guide 40. The detection redirection facet 38 may be coated with a reflective material. The detection guide 40 directs the detection light toward a detection output 42 and then toward a detector 44. According to one embodiment of the present invention, the light source 14 and detector 44 may be mounted inside an instrument, while the optical format 10 is located outside the instrument. In this embodiment, sample harvesting is easily accomplished and viewed by the patient, and the sample is kept outside the instrument where it does not contaminate the instrument or instrument optics.

In an optical format 10 according to the present invention, the alignment between the illumination light guide 18, the read window 32, and the detection guide 40 is fixed because each of these elements is a part of the optical format 10. According to one embodiment of the present invention, the cross-sectional area of the detection guide 40 is wider than that of the illumination light guide 18 to allow light that is less than perfectly collimated to be guided to the detector 44. Thus, the optical format includes within it a light pathway or waveguide that allows for uniform light travel and consistent readings when optically testing samples.

Turning now to FIG. 3, a top view of an optical format 10 according to the present invention is shown. In addition to the components described above, FIG. 3 shows one overillumination redirection facet 28 adapted to redirect a reference beam 46 for use in comparison to light that has passed through a sample. The reference beam is detected by a reference detector 48, and signal variation due to instability in the light source or thermal gradients can be corrected by taking a sample reading and a reference reading at the same time. A comparison of the sample to reference signals removes signal variation not caused by the sample 34.

Figure 4:
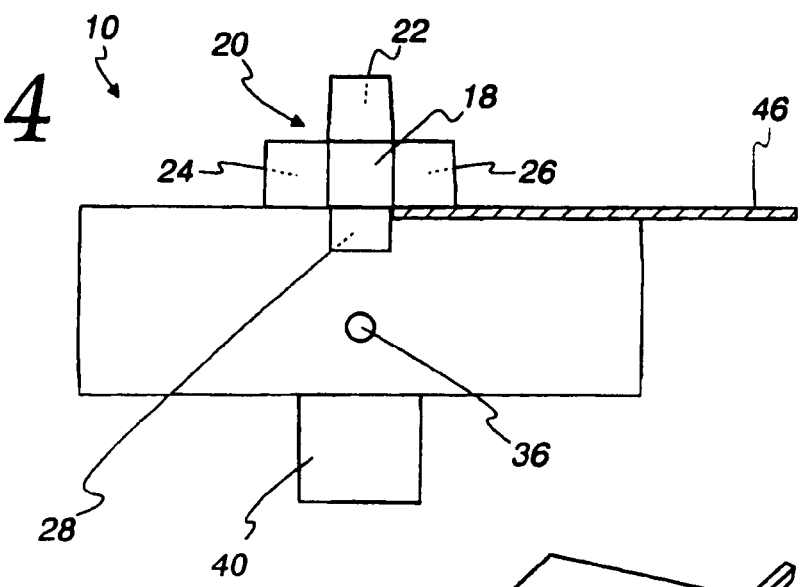
FIG. 4 is a front view of an optical format according to one embodiment of the present invention.
Figure 5:
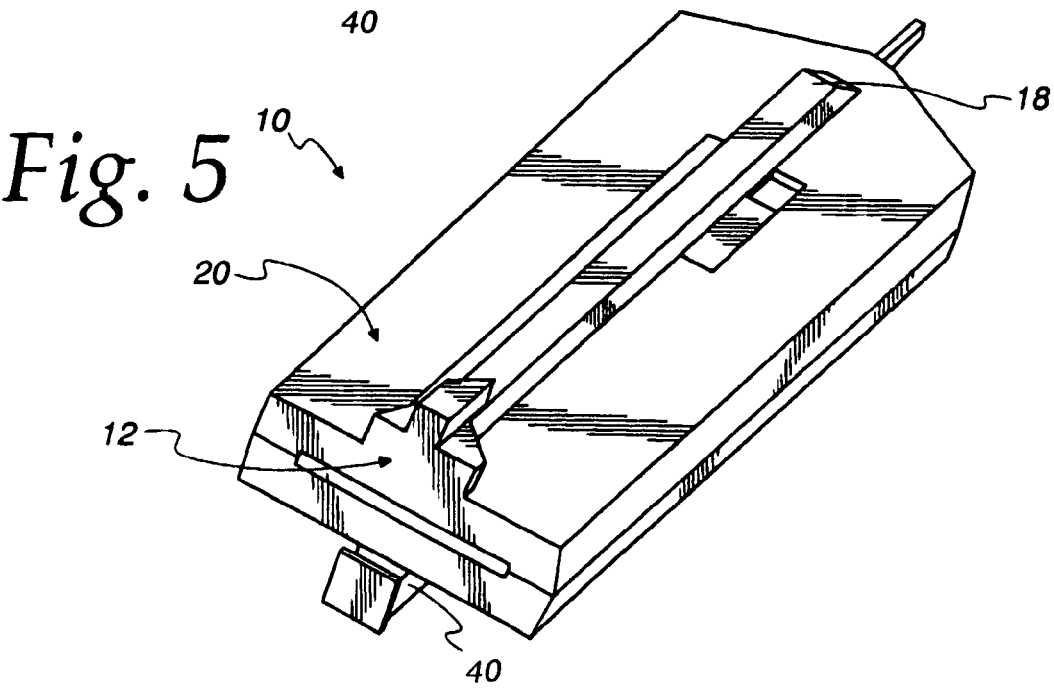
FIG. 5 is an isometric view of an optical format according to one embodiment of the present invention.

FIG. 4 shows a front view of an optical format 10 according to the present invention. FIG. 4 shows the reference beam 46 projecting perpendicularly from the axes of the illumination light guide 18 and the detection guide 40. An isometric view of an optical format 10 according to one embodiment of the present invention is shown in FIG. 5.

An optical format 10 of the present invention takes several elements that used to be disposed outside the format and brings them into a unitary construction which allows for a simpler overall construction. An optical format 10 according to the present invention may be molded of optically clear plastics, and may be molded in several separate snap-together parts which are joined during construction of the format. According to some embodiments of the present invention, the format 10 can be molded with optically clear materials such as acrylic, polycarbonate, and polyester. For ease of molding, all surfaces of an optical format 10 perpendicular to the normal optical axes may be given a draft of approximately 5 degrees.

Using the waveguided optical format 10 of the present invention, it is possible to allow an optimum optical read diameter of 0.75 mm while increasing the necessary mechanical tolerance between the format and optics to ±0.500 mm. Further, the ability to mold an optical format with optically clear plastics significantly decreases the complexity and cost of manufacturing an optical format. While an optical format 10 of the present invention may be scaled larger or smaller in size based on particular applications, according to one embodiment the illumination light guide 18 has a cross-sectional area of approximately 0.50 mm$^2$. With such an area, the location of an input light beam or the optical format 10 may be out of alignment by as much as ±0.5 mm before the illumination light guide 18 is filled with a less-than-acceptable amount of light. Including optical components within the format itself greatly enhances the consistency of optical sample readings, particularly when small sample volumes are used.

While the present invention has been described with reference to one or more particular embodiments, those skilled in the art will recognize that many changes may be made thereto without departing from the spirit and scope of the present invention. For example, while the present invention has been generally described as directed to medical applications it is to be understood that any optical fluid testing applications might employ the principles of the invention. Each of these embodiments and obvious variations thereof is contemplated as falling within the spirit and scope of the claimed invention, which is set forth in the following claims.

What is claimed is:

1. A format for optical analysis of samples, said format comprising:
   an illumination input area;
   an illumination light guide in optical communication with said illumination input area;
   a read window disposed approximately perpendicular to a longitudinal axis of said illumination light guide;
   a detection guide having one end proximate said read window and having a second end forming a detection output, said illumination light guide, said read window, and said detection guide defining a light pathway; and
   an overillumination redirection component located adjacent to and in optical communication with said illumination input area and said illumination light guide, said overillumination redirection component comprising four overillumination redirection facets disposed about an outside perimeter of said illumination light guide, said overillumination redirection facets configured to direct overilluminating light away from said light pathway.

2. The format of claim 1 further comprising an illumination redirection facet along said light pathway between said illumination input area and said read window, said illumination redirection facet configured to redirect illuminating light along said light pathway.

3. The format of claim 1 further comprising a detection redirection facet along said light pathway between said read window and said detection output, said detection redirection facet configured to redirect detection light along said light pathway.

4. The format of claim 1 further comprising a needle extending outwardly from said format and adapted to deposit a sample onto said read window.

5. The format of claim 1 further comprising a dried reagent on said read window.

6. The format of claim 1 wherein said illumination light guide has a first cross-sectional area and said detection guide has a second cross-sectional area, said second cross-sectional area being larger than said first cross-sectional area.

7. The format of claim 1 wherein said illumination light guide and said detection guide are molded of a unitary piece of optically clear material.

8. The format of claim 1 wherein said illumination light guide and said detection guide are molded of separate pieces of optically clear material joined into a single optical format.

9. The format of claim 1, wherein said overillumination redirection facets are configured to direct overilluminating light approximately perpendicular to said longitudinal axis of said illumination light guide.

10. The format of claim 9 wherein at least two of said overillumination redirection facets are disposed at an approximately 45-degree angle from said illumination light guide.

11. The format of claim 1 further comprising an illumination redirection facet along said light pathway between said illumination input area and said read window, and a detection redirection facet along said light pathway between said read window and said detection output.

12. A format for optical analysis of samples, said format comprising:
   an illumination input area;
   an illumination light guide in optical communication with said illumination input area, said illumination light guide comprising four sides defining an outside perimeter of said illumination light guide;
   a read window proximate to one end of said illumination light guide;
   a detection guide having one end proximate said read window and having a second end forming a detection output; and
   four overillumination redirection facets located proximate to and in optical communication with said illumination input area and said illumination light guide, said four overillumination redirection facets substantially surrounding said outside perimeter of said illumination light guide such that each overillumination redirection facet is adjacent to and in optical communication with a corresponding side of said illumination light guide.

13. The format of claim 12 wherein at least two of said overillumination redirection facets are disposed at approximately 45 degree angles from a longitudinal axis of said illumination light guide.

14. The format of claim 12 further comprising a needle extending outwardly from said format and adapted to deposit a sample onto said read window.

15. The format of claim 12 further comprising a dried reagent on said read window.

16. A format for optical analysis of samples, said format comprising:
    an illumination input area;
    an illumination light guide in optical communication with said illumination input area;
    a read window disposed along a light pathway;
    a detection guide having one end proximate said read window and having a second end forming a detection output, wherein said illumination light guide, said read window, and said detection guide define said light pathway; and
    four overillumination facets located adjacent to and in optical communication with said illumination input area and said illumination light guide, said overillumination facets disposed at acute angles relative to said light pathway and configured to direct overilluminating light away from said light pathway.

17. The format of claim 16 wherein said read window is disposed approximately perpendicular to a longitudinal axis of said illumination light guide.

18. The format of claim 16 wherein said detection guide is disposed approximately parallel to said illumination light guide.

19. A format for optical analysis of samples, said format comprising:
    an illumination light guide adjacent to an illumination input area, said illumination light guide having an outside perimeter;
    a detection guide having a first detection end proximate a read window and a second detection end forming a detection area;
    an overillumination redirection component proximate said illumination input area and substantially surrounding said outside perimeter of said illumination light guide, said overillumination redirection component comprising one or more overillumination redirection facets each disposed at an acute angle relative to a light pathway defined by said illumination light guide, said read window, and said detection guide such that said overillumination redirection component is configured to direct overilluminating light away from said light pathway.

20. The format of claim 19, wherein said illumination light guide has a polygonal cross-section comprising a plurality of sides that define said outside perimeter.

21. The format of claim 20, wherein each side borders a corresponding overillumination redirection facet.

22. The format of claim 19 wherein said read window is disposed approximately perpendicular to said light pathway.

23. The format of claim 19 wherein said overillumination redirection component is configured to direct overilluminating light approximately perpendicular to light pathway.

24. The format of claim 19 wherein said format further comprises an illumination redirection facet along said light pathway between said illumination input area and said read window, and a detection redirection facet along said light pathway between said read window and said detection area.

25. The format of claim 19 further comprising a needle extending outwardly from said format and adapted to deposit a sample onto said read window.

26. The format of claim 19 wherein said illumination light guide has a first cross-sectional area and said detection guide has a second cross-sectional area, said second cross-sectional area being larger than said first cross-sectional area.

27. The format of claim 19 wherein said illumination light guide and said detection guide are molded of a unitary piece of optically clear material.

28. The format of claim 19 wherein said illumination light guide and said detection guide are molded of separate pieces of optically clear material joined into a single optical format.

* * * * *

UNITED STATES PATENT AND TRADEMARK OFFICE
CERTIFICATE OF CORRECTION

PATENT NO. : 8,377,381 B2
APPLICATION NO. : 10/750271
DATED : February 19, 2013
INVENTOR(S) : Dosmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1878 days.

Signed and Sealed this
Thirtieth Day of December, 2014

Michelle K. Lee
*Deputy Director of the United States Patent and Trademark Office*